US012780789B2

(12) United States Patent
Cole et al.

(10) Patent No.: US 12,780,789 B2
(45) Date of Patent: Nov. 3, 2026

(54) METHOD OF CARBONYLATING AN EPOXIDE

(71) Applicant: Novomer LLC, Bainbridge, GA (US)

(72) Inventors: Branden Cole, Caledonia, NY (US); Jeff Uhrig, Media, PA (US)

(73) Assignee: Novomer LLC, Bainbridge, GA (US)

(*) Notice: Subject to any disclaimer, the term of this patent is extended or adjusted under 35 U.S.C. 154(b) by 509 days.

(21) Appl. No.: 18/282,915

(22) PCT Filed: Apr. 4, 2022

(86) PCT No.: PCT/US2022/023298
§ 371 (c)(1),
(2) Date: Sep. 19, 2023

(87) PCT Pub. No.: WO2022/221086
PCT Pub. Date: Oct. 20, 2022

(65) Prior Publication Data

US 2024/0166615 A1 May 23, 2024

Related U.S. Application Data

(60) Provisional application No. 63/175,736, filed on Apr. 16, 2021.

(51) Int. Cl.
*C07D 305/12* (2006.01)
*B01J 31/16* (2006.01)
*B01J 31/18* (2006.01)

(52) U.S. Cl.
CPC ........ *C07D 305/12* (2013.01); *B01J 31/1616* (2013.01); *B01J 31/183* (2013.01)

(58) Field of Classification Search
CPC .. B01J 31/1616; B01J 31/183; B01J 2231/00; B01J 2231/30; B01J 2231/34; B01J 2231/40; C07D 305/12; C07D 303/04
See application file for complete search history.

(56) References Cited

U.S. PATENT DOCUMENTS

| | | | | |
|---|---|---|---|---|
| 4,968,817 | A | 11/1990 | Brima | |
| 6,852,865 | B2 | 2/2005 | Coates et al. | |
| 8,481,756 | B1 | 7/2013 | Coates et al. | |
| 9,156,803 | B2 | 10/2015 | Allen et al. | |
| 9,327,280 | B2 | 5/2016 | Lee et al. | |
| 9,493,391 | B2 | 11/2016 | Allen et al. | |
| 10,245,559 | B2 | 4/2019 | Lapointe et al. | |
| 10,961,209 | B2 * | 3/2021 | Sookraj | B01J 29/46 |
| 2005/0014977 | A1 | 1/2005 | Drent et al. | |
| 2005/0240032 | A1 * | 10/2005 | Luinstra | C07D 315/00 549/328 |
| 2006/0257293 | A1 * | 11/2006 | Nguyen | B01J 19/18 422/198 |
| 2007/0213524 | A1 | 9/2007 | Coates et al. | |
| 2012/0123137 | A1 | 5/2012 | Allen et al. | |
| 2017/0029352 | A1 | 2/2017 | Sookraj et al. | |
| 2017/0096407 | A1 * | 4/2017 | Sookraj | B01J 31/2217 |
| 2018/0030015 | A1 * | 2/2018 | Farmer | B01J 31/00 |
| 2019/0047972 | A1 * | 2/2019 | Sookraj | B01J 37/024 |
| 2020/0391192 | A1 | 12/2020 | Yoon et al. | |

FOREIGN PATENT DOCUMENTS

| | | | | | |
|---|---|---|---|---|---|
| CN | 107428656 | A | * | 12/2017 | B01J 31/00 |
| WO | 2003050154 | A2 | | 6/2003 | |
| WO | 2010118128 | A1 | | 10/2010 | |
| WO | 2018067636 | A1 | | 4/2018 | |
| WO | 2020033267 | A1 | | 2/2020 | |
| WO | WO-2020033248 | A1 | * | 2/2020 | B01J 37/0207 |
| WO | 2021025918 | A2 | | 3/2021 | |

OTHER PUBLICATIONS

Machine translation of CN-107428656 (Year: 2017).*

International Preliminary Report on Patentability issued in co-pending International Application No. PCT/US2022/023298 mailed Jun. 30, 2023 (10 pages).

International Search Report and Written Opinion issued in co-pending International Application No. PCT/US2022/023298 mailed Aug. 25, 2022 (21 pages).

Written Opinion of the International Preliminary Examining Authority issued in co-pending International Appolication No. PCT/US2022/023298 mailed Feb. 27, 2023 (10 pages).

Park, Hoyoung D. et al., "Heterogeneous Epoxide Carbonylation by Cooperative Ion-Pair Catalysis in Co(CO)4-Incorporated Cr-MIL-101." 2017 American Chemical Society, 3, 444-448 (5 pages).

* cited by examiner

*Primary Examiner* — Katherine Zalasky Mcdonald

(57) ABSTRACT

A continuous method of carbonylating an epoxide and/or lactone with carbon monoxide with improved catalyst efficiency and reactor productivity is comprised of reacting the epoxy and/or lactone in a solvent with carbon monoxide in the presence of a catalyst at a temperature of at least 80° C. and an amount of water that is at most about 150 ppm of the effluent from the reactor. The amount of water in any of the ingredients used in a method of the invention is desirably substantially below the aforementioned water concentration in the effluent from the reactor. Likewise, in a method of the invention, the amount of polyether byproduct is substantially absent. The methods may be performed without recycling of the catalyst.

20 Claims, No Drawings

METHOD OF CARBONYLATING AN EPOXIDE

CROSS-REFERENCE TO RELATED APPLICATIONS

This application is a National Stage 371 entry of PCT/US2022/023298 filed on Apr. 4, 2022, published as WO 2022/221086, which claims priority to and the benefit of U.S. Provisional Patent Application Ser. No. 63/175,736 filed Apr. 16, 2021, both of which are incorporated herein by reference in their entirety for all purposes.

FIELD

The invention relates to improved carbonylation of an epoxide to form a carbonylation product such as a lactone or anhydride.

BACKGROUND

The catalyzed reactions of a gas with liquid reactant have typically been performed in stirred batch or continuously stirred reactors maintaining an overpressure of the reactant gas and continuous injection of the gas reactant into the liquid. Batch reactors tend to efficiently use the catalyst (i.e., have a high turnover number "TON" of the catalyst), but suffer from high capital costs for given throughput and down time between batches.

Continuously stirred reactors (CSTRs) may continuously produce product, but typically require increased loading of catalyst to realize desired productivity, requiring inefficient use of the catalyst. The inefficient use of catalyst is generally overcome by continually separating, recycling and replenishing the catalyst, which undesirably adds complexity and problems such as fouling of separation membranes and the like.

The continuous carbonylation of epoxides such as ethylene oxide employing recycling of a catalyst has been described in U.S. Pat. No. 9,493,391. In this patent various parameters are described for performing the reaction and suggests that the catalyst is deactivated at 90° C.

Accordingly, it would be desirable to provide a method of carbonylating an epoxide or lactone that avoids one or more of the problems of the prior art such as one described above.

SUMMARY

Applicant has surprisingly discovered that when carbonylating an epoxide or lactone at high temperatures in a CTSR, productivity may be maintained with lowered catalyst concentration with concomitant increase in TON (turnover number) without inactivating the catalyst by running/controlling the conditions such that the average water concentration is less than 150 ppm (parts per million by weight of the liquid effluent). Herein, for convenience, the epoxide and/or lactone within a solvent or without a solvent is referred to a "liquid reactants". Without being limiting in any way, it is believed that the reaction proceeds without formation of excess water or other undesired by products at higher temperatures when sufficient CO is present (i.e., avoids one or more side reactions). Likewise, it has been discovered that at high temperatures, the use of recycled catalyst, may introduce small concentrations of undesired products that may initiate and accelerate side reactions, decreasing the efficiency and productivity at higher operating temperatures.

A first aspect of the invention is a method of carbonylating an epoxide or lactone comprising reacting, continuously, the epoxide or lactone dissolved in a liquid solvent in the presence of carbon monoxide and a catalyst at a temperature of greater than 80° C. and a concentration of water of at most about 150 ppm to form a carbonylation product. The concentration of water is the amount of water present in the liquid effluent after the reactor reaches a steady state (e.g., after about 1 to 3 average residence time). The effluent typically contains, for example, the solvent, carbonylation product, catalyst, unreacted reactants (e.g., epoxide), and by-products (e.g., polyethers or aldehydes). As used herein the CO pressure is understood to mean the operating pressure of the reactor as described herein with the majority of the pressure arising from the CO.

A second aspect of the invention is a method of carbonylating an epoxide or lactone comprising, reacting the epoxide or lactone dissolved in a liquid solvent in the presence of carbon monoxide, a catalyst at a temperature of greater than 80° C., a carbon monoxide pressure of at least 700 psi and substantially in the absence of a byproduct polymer. The byproduct polymer is a polyether, polyester or polyetherester. The substantial absence of the byproduct polymer means the amount of such polymer is less than about 0.5% by weight of the effluent and desirably less than 0.1% by weight of the effluent. It has been discovered that at higher temperatures and pressures in the absence of recycling of the catalyst, the byproduct polymer may be minimized, which may act as initiators or growth centers for polymerization causing the reduction of the yield of the desired lactone or anhydride. A byproduct polymer herein is any oligomer or polymeric polyether, polyester or polyetherester that would be produced from the epoxide being carbonylated (e.g., ethylene oxide forms poly(ethylene oxide)). The amount of polyether may be determined by any suitable method such as known methods GPLC (gel permeation liquid chromatography), Infrared spectroscopy, nuclear magnetic residence and the like.

A third aspect of the invention is a method of carbonylating an epoxide or lactone, comprising reacting, continuously, the epoxide or lactone in a liquid solvent with carbon monoxide in the presence of a catalyst at a temperature of greater than 80° C., a carbon monoxide pressure of at least 700 psi, wherein the total water concentration of the epoxide, lactone, solvent and carbon monoxide (all of the components introduced into the reactor) is at most about 150 ppm. Desirably, the total water concentration of all the components introduced into the continuous reactor is at most about 100 ppm or 50 ppm (herein, "ppm" is parts per million by weight unless otherwise indicated). The use of dry reactants and components within the reactor allows for the efficient and practical continuous carbonylation of epoxides and lactones to form lactones and anhydrides respectfully at higher reaction temperatures and pressures.

The methods of the present invention improve the carbonylation of an epoxide, lactone or combination thereof by carbon monoxide. The invention enables the continuous carbonylation of an epoxide, for example, in a continuous stirred reactor without the need of recycling the catalyst while still realizing sufficient productivity and yield to minimize capital for practical production of lactones from the carbonylation of epoxides or carbonylation of lactones to form anhydrides.

DETAILED DESCRIPTION

The explanations and illustrations presented herein are intended to acquaint others skilled in the art with the invention, its principles, and its practical application. The specific embodiments of the present disclosure as set forth are not intended to be exhaustive or limit the scope of the disclosure.

The method is directed to the carbonylation of an epoxide or lactone dissolved in a solvent with carbon monoxide in the presence of a catalyst at a temperature of at least 80° C. It has been surprisingly discovered, without being limiting in any way, that under the proper conditions, improved productivity and turnover numbers (TONS) may be realized by avoiding excess water concentrations, which may result in catalyst inactivation and increased side reactions. This allows for the commercial practicable method without the use of recycling of the catalyst, which is believed to introduce contaminants into the reaction causing lowered yield of the desired lactone or anhydride due increased initiation of undesired byproducts such as byproduct polymers.

The epoxide or lactone may be any suitable epoxide or lactone such as those known in the art. Substituted epoxides (i.e., "oxiranes") include monosubstituted oxiranes, disubstituted oxiranes, trisubstituted oxiranes, and tetrasubstituted oxiranes. Such epoxides may be further optionally substituted. In some embodiments, epoxides comprise a single oxirane moiety. In some embodiments, epoxides comprise two or more oxirane moieties. The lactone may be any lactone such as those produced when carbonylating the aforementioned epoxides. Examples of such epoxides and lactones include ethylene oxide, propylene oxide and their corresponding lactone carbonylation products beta propiolactone and beta butyrolactone. Examples of such lactones include beta propiolactone and beta butyrolactone and their corresponding carbonylation products succinic anhydride and methylsuccinic anhydride. Further examples of epoxides and lactones are in Table A (between paragraphs 65 and 66) of PCT Pub. WO2020/033267 incorporated herein by reference.

The epoxide or lactone is mixed with, entrained in, or dissolved in a solvent. Any useful solvent may be used. The solvent may be used to enhance, for example, the presence of the gas reactant with the epoxide or lactone. As an illustration, the solvent may be an organic solvent such as an aliphatic hydrocarbon, aromatic hydrocarbon, aprotic polar solvent, halogenated solvent, ether, ester, ketone, nitrile, amide, carbonate, alcohol, amine, sulfone, mixture thereof or combination thereof. Exemplary solvents may include diethyl ether, methyl tertbutyl ether, tetrahydrofuran, 1,4-dioxane, glyme, diglyme, triglyme, higher glymes, tetrahydropyran, 2,5-dimethyl tetrahydrofuran, sulfolane, N-methyl pyrrolidone, 1,3 dimethyl-2-imidazolidinone, tetraglyme, diethylene glycol dibutyl ether, isosorbide ethers, diphenyl ether, ethylene carbonate, propylene carbonate, butylene carbonate, dibasic esters, acetonitrile, ethyl acetate, propyl acetate, butyl acetate, 2-butanone, cyclohexanone, toluene, difluorobenzene, dimethoxy ethane, acetone, methylethyl ketone, or mixtures thereof. The amount of solvent may be any useful amount for performing the method and may vary over a wide range. For example, the amount of solvent to epoxide or lactone by weight (solvent/(epoxide or lactone)) may vary from 1, 10 or 20 to 99, 90, or 80.

The epoxide or lactone is carbonylated using carbon monoxide in the presence of catalyst. The carbon monoxide may be provided by itself (other than contaminants) or mixed with other gases. For example, the carbon monoxide may be mixed with one or more other gases such as nitrogen or inert gases (e.g., noble gas). The carbon monoxide may also be mixed with hydrogen such as in a commercially available syngas.

The catalyst may be a homogeneous catalyst, heterogeneous catalyst or combination thereof. The catalyst may be a homogeneous catalyst dissolved, mixed with or entrained with the epoxide and/or with or without solvent. The catalyst may be a heterogeneous catalyst. The heterogeneous catalyst may be present as a particle in the liquid reactant (slurry) prior to insertion into the reactor. The heterogenous catalyst that is anchored to a support, which may be used as the packing in a plug flow reactor. As an illustration, the heterogeneous catalyst may be supported catalyst useful in the carbonylation of epoxides or lactones such as described in copending application PCT/US2020/044013 incorporated herein by reference. The support may be a porous ceramic such as a packing bead described above and, in an embodiment, may be a zeolite such as described in paragraph 36 of said copending application incorporated herein by reference, silica, titania, silver (e.g., silver in clay binder). Other exemplary catalysts for carbonylation of epoxides or lactones are described in U.S. Pat. Nos. 6,852,865 and 9,327,280 and U.S. Pat. Appl. Nos. 2005/0014977 and 2007/0213524 each incorporated herein by reference.

The catalyst desirably is a homogeneous metal carbonyl catalyst. The metal carbonyl catalyst may be represented by [QMy(CO)w]x where: Q is any ligand; M is a metal atom; y is an integer from 1 to 6 inclusive; w is a number that renders the metal carbonyl stable; and x is an integer from −3 to +3 inclusive. M may be Ti, Cr, Mn, Fe, Ru, Co., Rh, Ni, Pd, Cu, Zn, Al, Ga or In and desirably Co. The metal carbonyl catalyst may be anionic and further comprised of a cationic Lewis acid. The cationic Lewis acid may be a metal complex represented by [MT(L)b]c+, where, M' is a metal; each L is a ligand; b is an integer of 1 to 6; c is 1, 2, or 3; and where, if more than one L is present, each L may be the same or different. The ligand L may be a dianionic tetradentate ligand. The dianionic tetradentate ligand may be a porphyrin derivative, salen derivative, dibenzotetramethyltetraaza 14 annulene ("TMTAA) derivative; phthalocyaninate derivative, derivative of the Trost ligand or combination thereof. Desirably, the dianionic tetradentate ligand is a porphyrin derivative. M' may be a translation metal or group 13 metal. Desirably, M' may be aluminum, chromium, indium, gallium or combination thereof and in particular M' is aluminum, chromium or combination thereof.

The carbon monoxide, solvent, epoxide or lactone individually or in total that are injected into a reactor desirably have a water content that is at most about 150 parts per million by weight (ppm). Generally, it is desirable for the carbon monoxide, solvent, epoxide or lactone individually or in total (e.g. combination of solvent, carbon monoxide, and epoxide, lactone or both) to a have at most about 100 ppm, 50 ppm, 40 ppm, 30 ppm, 25, ppm, 15 ppm, 10 ppm or 5 ppm of water. The concentration of water in the solvent, epoxide or lactone may be lowered by any suitable method for removing water from a liquid or gas such as those known in the art. Exemplary methods include distillation, Joule-Thomson expansion, liquid or solid desiccants and the like or combination thereof.

The reactants (epoxide, lactone, carbon monoxide), solvent and catalyst may be introduced into any suitable continuous reactor such as a continuously stirred reactor or plug flow reactor such as those known in the art and desirably a vertical plug flow reactor. A particularly useful reactor is the hybrid bubble plug flow reactor described in copending U.S. provisional application No. 63/143,348, "IMPROVED REACTOR AND METHOD FOR REACTING A GAS AND LIQUID REACTANTS," with inventors Branden Cole and Jeff Uhrig filed on Jan. 29, 2021. The liquid reactants, solvent and CO may be introduced into the reactor by any suitable means. For example, each of the reactants, solvent and CO may be separately introduced or be premixed in any combination that may be desired. As an illustration, the solvent, catalyst and liquid reactant (e.g., epoxide) are mixed prior to introduction into the reactor and the CO is bubbled into the liquid at sufficient rate so as to limit side reactions that may lead to reduction in yield or catalyst deactivation due to CO starvation.

The CO may be injected into the reactor at any useful rate to realize the desired catalyst TON and reactor productivity. Typically, the molar ratio (or equivalent ratio) of the CO/liquid reactant (e.g., epoxide and/or lactone) is greater than 1, 1.1. 1.2, 1.4 or 1.5 to about 20, 10, 7, 5, 4 or 3. It is believed, without being limiting in any way, that the excess of gas reactant allows for maintaining of the concentration of the CO throughout the residence time within the reactor so as to avoid starvation of the gas reactant in the reactor. Likewise, excess amounts of gas reactant that results in saturation, is believed, without being limiting may cause evaporation of the liquid reactant, product or solvent into the bubbles formed within the liquid reactant and thus inhibiting the catalyzed reaction.

The residence time of the reactor may be any useful time for performing the carbonylation. The residence time, illustratively, may range from 1 minute, 5 minutes, 10 minutes, 20 minutes or 30 minutes to several hours (3 to 5), 240 minutes, 180 minutes, 120 minutes, or 90 minutes. More than one reactor may be employed in series or parallel. When reactors are employed in series, they may each have an individual residence time as just described. The total residence time of the series reactors may be any combination of residence times of the individual reactors, but desirably, the total residence time of the series reactors falls within the times described in this paragraph.

Desirably, the bubbles that are formed in the liquid reactant are of a size that enhances the dissolution and maintenance of the concentration within the liquid solvent and reactant (epoxide and/or lactone) and even distribution throughout the reactor. A sparger may be used when injecting the gas reactant. The sparger may be any commonly used in the chemical or biochemical industries. For example, the sparger may be a porous sintered ceramic frit or porous metal frit such as those available from Mott Corp. Farmington, CT. The pore size of the porous sintered frit sparger may be any useful such as those having a pore size of 0.5 micrometer, 1 micrometer, 2 micrometers to 100 micrometer, 50 micrometers, 20 micrometers or 15 micrometers. Examples of other gas spargers that may be suitable include perforated plate, needle, spider, or combination thereof of varying sized openings depending on the desired gas bubble size. Likewise, in a CSTR the bubble size desired may be facilitated by the degree of agitation and agitator used. The bubble size desired may also be facilitated by the use of a surface active agent including but not limited to ionic (cationic, anionic, and amphoteric surfactants) or nonionic surfactants that are separately added. The surface active agent may be entrained in the solvent and epoxide when inserted or be separately inserted into the reactor. In an embodiment, the surface active agent may be insitu produced as a by product in a controlled manner. For example, a glycolic oligomer may be produced when carbonylating an epoxide or lactone with carbon monoxide so long as an excess is not produced that deleteriously affects the productivity of the reactor or TON of the catalyst.

The amount of water when reacting is determined from the effluent of the continuous reactor such as CSTR after the reactor reaches a steady state (e.g., after about the average reaction residence time). Generally, the concentration of water in the liquid effluent is at most about 150 ppm and desirably is at most about 125 ppm, 110 ppm, 100 ppm, 90 ppm, 80 ppm, 70 ppm, 60 ppm, 50 ppm to a trace amount of water, 1 ppm or 5 ppm of water. The amount of water in the effluent or any component added to the reactor (e.g. liquid reactants, solvent, CO, and catalyst) may be determined by any suitable method such as those known in the art. Exemplary methods may include Karl Fischer titration, gas chromatography/mass spectrometry-select ion monitoring/thermal conductivity detection, infrared spectroscopy, and the like.

The temperature of the reaction is carried out at a temperature of at least 80° C. and a sufficient pressure of CO and low catalyst concentration (e.g., sufficiently high epoxide/catalyst molar ratio) to realize the improved TON and reactor productivity. It is believed, without being limiting in any way, that to realize method without premature catalyst inactivation and reduced side reactions, sufficient pressure at elevated temperatures facilitates the desired productivity and TONs. The elevated pressure is believed to suppress side reactions by maintaining a minimum threshold pressure of CO at the catalyst reaction site decreasing the deleterious effect of water on the catalyst and reaction pathway. Generally, the operating pressure is at least about 700 psi within the reactor. Desirably, the pressure is at least 800 psi, 900 psi, 1000 psi or 1100 psi to any practicable pressure such as 2000 or 3000 psi. It is understood that the operating pressure includes other species such as ethylene oxide or nitrogen, but generally at least about 80% or 90% of the gas is carbon monoxide.

Even though a reaction temperature of about 80° C. may be sufficient, it has been discovered that even higher temperatures may be desirable to realize the desired TONs and productivity without having to recycle catalyst while still avoiding excess formation of water particularly at higher CO pressures as described above. Generally, the reaction temperature may be at least about 85° C., 90° C., 95° C., 100° C., 105° C., 110° C., 115° C., or 120° C. to about 130° C.

To realize the desired TONs and reactor productivity, generally, the concentration of the catalyst is sufficiently low, which is believed without being limiting, to minimize undesired side reactions or the production of water. Typically, the concentration of catalyst as given by the molar or equivalent ratio of liquid reactant/catalyst (liquid reactant being the epoxide, lactone or combination thereof as previously described). Desirably, the reactant is the epoxide and the reactant/catalyst molar ratio is the epoxide/catalyst ratio. The ratio is understood to mean the reactant/catalyst ratio of the epoxide and/or lactone and catalyst introduced into the continuous reactor (i.e., CSTR or plug flow reactor). Generally, the reactant/catalyst ratio is at least 1500 or greater and may be 1750, 2000, 2200, 2500 or 2800 to about 50,000, 25,000 or 20,000. The reactant may be added along the length of a plug flow reactor if desired.

The methods for reacting an epoxide and lactone of the present invention realizes surprisingly high TONs of the catalyst and reactor productivity at low concentrations of catalyst. Turnover Number (TON) is used as commonly understood in the art for continuous reactions, where the amount of catalyst and product produced in a given time results in the TON for continuous reactions and is given by (moles product/time)/(moles catalyst/time). TONs indicate the efficacy of the catalyst for continuous reactions where the output of the product is similar. The productivity is given by the amount of product produced in a given time in a given reactor volume (moles product/(time×volume)). This surprising result allows for continuous carbonylation of an epoxide and/or lactone without the need for recycling of the catalyst. The TONs are desirably at least about 1500, 2000, 3000, 4000, 5000, 7500, 9000 or even 10,000 to any practicable amount such as 50,000 (moles product/minute)/(moles catalyst/min). The productivity even though the catalyst concentration is decreased may be maintained or even increased. The productivity desirably is at least about $1\times10^{-8}$, $5\times10^{-8}$, or $1\times10^{-7}$ moles product/s·mL to any practical productivity.

Illustrative Embodiments

The following examples are provided to illustrate the method and reactor without limiting the scope of the invention. All parts and percentages are by weight unless otherwise noted.

Examples 1-19 and Comparative Examples 1-17

A 2 liter high pressure lab scale continuous stirred reactor constructed of 316 stainless steel available from Parker/Autoclave Engineers (Pennsylvania) and stirred at 2000 rpm is used for each of Examples 1-19 and Comparative Examples 1-17. The reactants (feed) and run conditions for each Example and Comparative Example is shown in Table 1. The catalyst used in each of these Examples and Comparative Examples is meso-tetraphenylporphryrin Al bis (THF) tetracarbonyl cobaltate. The results from each Example and Comparative Example is shown in Table 2. In Table 2, ACH is acetaldehyde byproduct, bPL is beta propiolactone, SAH is succinic anhydride, PPL is polypropiolactone, PEG is polyether glycol The results are determined from the effluent after the reactor has reached steady state (e.g., at least about 1 residence time) and the reactor is run over several residence times. The THF (tetrahydrofuran), ethylene oxide (EO) and carbon monoxide (CO) combined had a total water concentration of about 20 to 40 ppm. The TON is determined by measuring the moles of product produced (beta propiolactone "bPL") divided by the amount of moles of catalyst put into the reactor ((mol. product/min)/(mol. cat./min)). The productivity is determined by measuring the moles of product produced per minute divided by the reactor volume ((mol. product/min)/reactor volume in ml).

The composition of the effluent is determined by an Agilent 7890A GC/TCD (gas chromatography/thermal conductivity detection (GC/TCD) other than the any byproduct polymer such as polyethylene glycol (PEG) and polypropiolactone (PPL). The PEG and PPL are determined by NMR analysis via Varian Mercury operating at 300 MHz.

Comparative Examples 18-20

Comparative Examples 18-20 are run at 70° C., 900 psi, catalyst concentration of 1.66 mM in the reactor, and 60 minute residence time in the same manner and reactor as Examples 1-19 except that the total water feed is varied as shown in Table 3. The results are shown in Table 3. These results indicate that even at reaction conditions that do not product substantial amounts of water, the feed water concentration causes an increase in undesirable by products such as byproduct polymers (e.g., polypropiolactone (PPL) and polyethylene oxide (PEO).

TABLE 1

| Example | T (° C.) | P (psi) | Res Time (min) | THF feed rate (g/min) | EO Feed Rate (g/min) | EO/CAT Molar Ratio |
|---|---|---|---|---|---|---|
| Comp. 1 | 110 | 700 | 60 | 9 | 2.12 | 927 |
| 1 | 110 | 1100 | 120 | 3.47 | 2.2 | 7563 |
| Comp. 2 | 50 | 700 | 120 | 3.47 | 2.2 | 7563 |
| 2 | 80 | 900 | 90 | 5.14 | 2.09 | 2181 |
| Comp. 3 | 110 | 700 | 120 | 3.37 | 2.19 | 1951 |
| Comp. 4 | 80 | 900 | 90 | 5.46 | 2.09 | 2186 |
| Comp. 5 | 50 | 700 | 60 | 6.73 | 4.39 | 1920 |
| Comp. 6 | 110 | 1100 | 60 | 6.73 | 4.39 | 1920 |
| Comp. 7 | 110 | 1100 | 120 | 4.5 | 1.06 | 944 |
| Comp. 8 | 50 | 1100 | 120 | 3.37 | 2.19 | 1951 |
| Comp. 9 | 50 | 1100 | 120 | 3.37 | 2.19 | 1951 |
| Comp. 10 | 50 | 700 | 120 | 4.5 | 1.06 | 944 |
| Comp. 11 | 50 | 1100 | 60 | 9 | 2.12 | 927 |
| 3 | 80 | 900 | 90 | 5.46 | 2.09 | 2186 |
| 4 | 110 | 700 | 60 | 6.93 | 4.4 | 7792 |
| 5 | 110 | 700 | 120 | 4.6 | 1.06 | 3644 |
| 6 | 110 | 1100 | 60 | 9.21 | 2.13 | 3772 |
| Comp. 12 | 50 | 700 | 120 | 3.47 | 2.2 | 7563 |
| 7 | 80 | 900 | 90 | 5.14 | 2.09 | 2181 |
| Comp. 13 | 50 | 1100 | 60 | 6.93 | 4.4 | 7792 |
| Comp. 14 | 50 | 700 | 60 | 9.21 | 2.13 | 3772 |
| 8 | 80 | 900 | 90 | 5.14 | 2.09 | 2181 |
| Comp. 15 | 50 | 1100 | 120 | 4.6 | 1.06 | 3644 |
| 9 | 100 | 1100 | 60 | 10.53 | 0.9 | 15340 |
| 10 | 100 | 1100 | 120 | 5.26 | 0.45 | 15340 |
| 11 | 115 | 1100 | 120 | 5.26 | 0.45 | 15340 |
| 12 | 100 | 1100 | 180 | 5.26 | 0.45 | 15340 |
| Comp. 16 | 70 | 1100 | 120 | 6.8 | 1.5 | 1753 |
| Comp. 17 | 70 | 1100 | 270 | 3.4 | 0.7 | 3272 |
| 13 | 110 | 1100 | 120 | 4.82 | 0.756 | 24916 |
| 14 | 100 | 1100 | 120 | 5.23 | 0.363 | 12406 |
| 15 | 110 | 1100 | 240 | 3.44 | 0.263 | 12299 |
| 16 | 100 | 1100 | 240 | 3.12 | 0.546 | 24500 |
| 17 | 105 | 1100 | 180 | 2.87 | 0.345527 | 4165 |
| 18 | 105 | 1100 | 180 | 3.17 | 0.501226 | 19205 |
| 19 | 100 | 1100 | 60 | 10.53 | 0.9 | 15340 |

TABLE 2

| | Effluent | | | | | | | | Productivity |
|---|---|---|---|---|---|---|---|---|---|
| Example | ACH | EO | bPL | SAH | PPL | PEG | Water (ppm) | TON | (mols product/ second * mL |
| Comp. 1 | 3.00% | 0.20% | 15.00% | 3.00% | | | 460 | 483 | 5.38E-07 |
| 1 | 1.60% | 6.50% | 31.00% | 0.20% | | | 42 | 3898 | 5.52E-07 |
| Comp. 2 | 0.03% | 16.00% | 12.00% | 0.00% | | | 14 | 1272 | 1.8E-07 |
| 2 | 0.17% | 1.50% | 34.00% | 0.12% | | | 16 | 1917 | 8.95E-07 |
| Comp. 3 | 4.10% | 6.70% | 23.00% | 0.21% | 1.40% | | 290 | 701 | 3.83E-07 |
| Comp. 4 | 0.24% | 1.70% | 32.00% | 0.19% | | | 18 | 1760 | 8.2E-07 |
| Comp. 5 | 0.07% | 10.00% | 14.00% | 0.23% | | 15.00% | 12 | 445 | 4.96E-07 |

TABLE 2-continued

| | Effluent | | | | | | | | Productivity |
|---|---|---|---|---|---|---|---|---|---|
| Example | ACH | EO | bPL | SAH | PPL | PEG | Water (ppm) | TON | (mols product/ second * mL |
| Comp. 6 | 2.20% | 5.80% | 30.00% | 0.21% | 3.80% | | 230 | 1000 | 1.11E−06 |
| Comp. 7 | 3.80% | 0.27% | 14.00% | 3.50% | 1.10% | | 350 | 467 | 2.56E−07 |
| Comp. 8 | 0.13% | 7.20% | 19.00% | 0.00% | | 17.00% | 15 | 660 | 3.61E−07 |
| Comp. 9 | 0.11% | 9.30% | 16.00% | 0.00% | | 16.00% | 14 | 537 | 2.94E−07 |
| Comp. 10 | 0.15% | 0.48% | 24.00% | 0.14% | | | 9 | 824 | 4.51E−07 |
| Comp. 11 | 0.14% | 2.30% | 18.00% | 0.00% | | 1.50% | 0 | 585 | 6.52E−07 |
| 3 | 0.33% | 1.80% | 33.00% | 0.19% | | | 0 | 1849 | 8.61E−07 |
| 4 | 3.10% | 11.00% | 22.00% | 0.70% | | | 107 | 2730 | 7.51E−07 |
| 5 | 2.00% | 2.10% | 19.00% | 0.25% | | | 150 | 2480 | 3.51E−07 |
| 6 | 1.50% | 1.90% | 20.00% | 0.24% | | | 62 | 2700 | 7.43E−07 |
| Comp. 12 | 0.02% | 19.80% | 5.05% | 0.00% | | | 6.2 | 513 | 7.27E−08 |
| 7 | 0.23% | 1.99% | 30.18% | 0.16% | | | 23 | 1620 | 7.56E−07 |
| Comp. 13 | 0.06% | 15.00% | 8.00% | 0.00% | 0.40% | 2.20% | 7.4 | 844 | 2.32E−07 |
| Comp. 14 | 0.06% | 9.93% | 7.43% | 0.00% | | | 7 | 927 | 2.55E−07 |
| 8 | 0.23% | 1.70% | 34.75% | 0.17% | | | 19 | 1992 | 9.3E−07 |
| Comp. 15 | 0.03% | 11.50% | 7.18% | 0.00% | | | 5 | 883 | 1.25E−07 |
| 9 | 0.15% | 3.00% | 5.30% | 0.00% | | | | 6493 | 1.86E−07 |
| 10 | 0.14% | 2.70% | 6.10% | 0.00% | | | | 7507 | 1.07E−07 |
| 11 | 0.70% | 1.40% | 8.00% | 0.06% | | | | 9979 | 1.43E−07 |
| 12 | 0.23% | 2.40% | 8.10% | 0.00% | | | | 10168 | 9.24E−08 |
| Comp. 16 | 0.07% | 0.90% | 18.20% | 0.10% | | | | 1172 | 2.97E−07 |
| Comp. 17 | 0.05% | 3.60% | 19.20% | 0.03% | | | | 2504 | 1.59E−07 |
| 13 | 0.81% | 3.00% | 11.00% | 0.12% | | | | 12887 | 1.91E−07 |
| 14 | 0.21% | 1.10% | 7.20% | 0.04% | | | | 8790 | 1.25E−07 |
| 15 | 0.73% | 0.51% | 9.00% | 0.19% | | | | 11118 | 7.39E−08 |
| 16 | 0.52% | 2.97% | 15.98% | 0.56% | | | | 19595 | 1.35E−07 |
| 17 | 0.81% | 0.69% | 14.00% | 0.29% | | | | 3924 | 1.59E−07 |
| 18 | 0.84% | 2.60% | 16.00% | 0.08% | | | | 15274 | 1.94E−07 |
| 19 | 0.37% | 3.36% | 5.90% | 0.00% | | | | 7323 | 2.09E−07 |

TABLE 3

| Example | Total Water in Feed | bPL % | EO % | TON | PPL Wt % | PEO Wt % |
|---|---|---|---|---|---|---|
| Comp. 18 | 18 | 20.60% | 3.10% | 1534 | 0.04% | 0.41% |
| Comp. 19 | 51 | 19.10% | 3.50% | 1402 | 0.07% | 1.00% |
| Comp. 20 | 115 | 17.20% | 4.60% | 1249 | 0.06% | 1.01% |

What is claimed is:

1. A method of carbonylating a reactant that is an epoxide, lactone or combination thereof comprising reacting, continuously, the reactant in a liquid solvent with carbon monoxide in the presence of a catalyst at a temperature of at least 85° C. to at most 130° C., a carbon monoxide pressure of 700 psi to 2000 psi to form a carbonylation product in an effluent having a concentration of water of at most 150 ppm, the catalyst being present at a molar ratio of reactant/catalyst greater than 2000 and the carbonylating having a turnover number of at least about 1500.

2. The method of claim 1, wherein the pressure is at least 800 psi, the temperature is at least 90° C., the molar ratio of CO/reactant is from 1.2 to 20, and the reactant and catalyst are present in amounts such that the reactant and catalyst have a molar ratio of reactant/catalyst from 2200 to 25,000.

3. The method of claim 2, wherein the pressure is at least 1000 psi and the temperature is at least 100° C.

4. The method of claim 1, wherein the reactant is an epoxide and the epoxide is ethylene oxide, propylene oxide or combination thereof.

5. The method of claim 1, wherein the catalyst is comprised of a homogeneous catalyst, and the solvent is an ether, hydrocarbon, aprotic polar solvent or mixture thereof.

6. The method of claim 5, wherein the catalyst is a metal carbonyl catalyst, represented by [QMy(CO)w]x where: Q is any ligand; M is a metal atom; y is an integer from 1 to 6 inclusive; w is a number that renders the metal carbonyl stable; x is an integer from −3 to +3 inclusive.

7. The method of claim 6, wherein the metal carbonyl catalyst is anionic and further comprised of a cationic Lewis acid, wherein the cationic Lewis acid is a metal complex represented by [M'(L)b]c+, where, M' is a metal; each Lis a ligand; b is an integer of 1 to 6; c is 1, 2, or 3; and where, if more than one L is present, each L may be the same or different.

8. The method of claim 7, wherein the ligand L is a dianionic tetradentate ligand, and M' is a translation metal or group 13 metal.

9. The method of claim 8, wherein the dianionic tetradentate ligand is a porphyrin derivative; and wherein M' is aluminum, chromium, indium, gallium or combination thereof.

10. The method of claim 1, wherein the method is performed in a continuously stirred reactor or plug flow reactor.

11. The method of claim 5, wherein the solvent is, tetrahydrofuran, tetrahydropyran, 2,5-dimethyl tetrahydrofuran, sulfolane, N-methyl pyrrolidone, 1,3 dimethyl-2-imidazolidinone, diglyme, triglyme, tetraglyme, diethylene glycol dibutyl ether, isosorbide ethers, methyl tertbutyl ether, diethyl ether, diphenyl ether, 1,4-dioxane, ethylene carbonate, propylene carbonate, butylene carbonate, dibasic esters, acetonitrile, ethyl acetate, propyl acetate, butyl acetate, 2-butanone, cyclohexanone, toluene, difluorobenzene, dimethoxy ethane, acetone, methylethyl ketone, or mixture thereof.

12. The method of claim 11, wherein the solvent is comprised of THF.

13. The method of claim 1, wherein the concentration of water is at most about 75 ppm.

14. The method of claim 1, wherein any one or more of the reactant, solvent, and carbon monoxide are dried prior to reacting.

15. The method of claim 1, wherein the method is performed in a plug flow reactor, wherein the plug flow reactor is a vertical plug flow reactor, wherein the solvent, catalyst and reactant are mixed prior to introduction into the reactor and carbon monoxide (CO) is bubbled into the liquid at sufficient rate so as to limit side reactions and the molar ratio of CO/reactant is from 1.2 to 20.

16. The method of claim 1, wherein the carbonylation product is a beta lactone in the substantial absence of an anhydride.

17. A method of carbonylating a reactant that is an epoxide, lactone or combination thereof, comprising reacting, continuously the reactant in a liquid solvent with carbon monoxide in the presence of a catalyst at a temperature of at least 85° C., a carbon monoxide pressure of at least 700 psi, the catalyst being present at a molar ratio of reactant/catalyst greater than 2000, to form a carbonylation product in an effluent, the effluent being substantially in the absence of a by product polymer and having a water concentration of at most 150 ppm and the carbonylating has a turnover number of at least about 1500.

18. The method of claim 17, wherein the reacting is performed in the absence of recycling of the catalyst; and the concentration of the by product polymer is comprised of a polyether that is present in an amount of at most 0.2% by weight.

19. A method of carbonylating a reactant that is an epoxide, lactone or combination thereof, comprising reacting, continuously the reactant in a liquid solvent with carbon monoxide in the presence of a catalyst at a temperature of at least 85° C., a carbon monoxide pressure of at least 700 psi, to form a carbonylation product in an effluent, the effluent having a water concentration of at most 150 ppm, wherein the reactant, carbon monoxide and solvent have a total water concentration of at most 40 ppm, the catalyst being present at a molar ratio of reactant/catalyst greater than 2000 and the carbonylating has a turnover number of at least about 1500.

20. The method of claim 19, wherein the total water concentration is at most 20 ppm.

* * * * *